(12) United States Patent
Zieker

(10) Patent No.: US 9,075,067 B2
(45) Date of Patent: Jul. 7, 2015

(54) MARKER FOR THE DIAGNOSIS OF CANCER

(75) Inventor: Derek Zieker, Tuebingen (DE)

(73) Assignee: EBERHARD-KARLS-UNIVERSITAET TUEBINGEN, Tuebingen (DE)

(*) Notice: Subject to any disclaimer, the term of this patent is extended or adjusted under 35 U.S.C. 154(b) by 524 days.

(21) Appl. No.: 12/753,686

(22) Filed: Apr. 2, 2010

(65) Prior Publication Data

US 2010/0247432 A1    Sep. 30, 2010

Related U.S. Application Data

(63) Continuation of application No. PCT/EP2008/008322, filed on Oct. 1, 2008.

(30) Foreign Application Priority Data

Oct. 2, 2007  (DE) .......................... 10 2007 048 636

(51) Int. Cl.
| | |
|---|---|
| *C12Q 1/68* | (2006.01) |
| *A61K 45/06* | (2006.01) |
| *G01N 33/574* | (2006.01) |
| *A61K 31/713* | (2006.01) |
| *A61K 39/395* | (2006.01) |

(52) U.S. Cl.
CPC ........ G01N 33/57446 (2013.01); C12Q 1/6886 (2013.01); *C12Q 2600/118* (2013.01); *C12Q 2600/158* (2013.01); A61K 45/06 (2013.01); A61K 31/713 (2013.01)

(58) Field of Classification Search
CPC ................. G01N 33/57446; C12Y 207/02003; C12Y 207/0201
See application file for complete search history.

(56) References Cited

FOREIGN PATENT DOCUMENTS

| WO | WO 2005/001126 A1 | 1/2005 |
|---|---|---|
| WO | WO 2007/065010 A2 | 6/2007 |

OTHER PUBLICATIONS

Taber's Cyclopedic Medical Dictionary (1985, F.A. Davis Company, Philadelphia, p. 274).*
Kaiser (Science, 2006, 313: 1370).*
Krontiris and Capizzi (Internal Medicine, 4th Edition, Editor-in-chief Jay Stein, Elsevier Science, 1994 Chapters 71-72, pp. 699-729).*
Wilmanns et al. (Cancer Metastasis Rev. 2012 31: 269-276).*
Pritzker (Clinical Chemistry, 2002, 48:1147-1150).*
Kress et al. (J. Cancer Res. Clin. Oncol. 1998 124: 315-320).*
Kufe et al. (NCBI-Bookshelf, Holland-Frei Cancer Medicine, 6th ed., Hamilton (ON): BC Decker, 2003).*
Valcarcel et al. (98th AACR Annual Meeting Apr. 14-18, 2007, Abstract #2549).*
Ma et al. (World Chinese J. Digestology Jun. 2006 14: 1566-1570, Abstract).*
Hwang et al. (Proteomics 2006 6: 2259-2272).*
Han et al. (Clin. Oncology 2006 18:761-767).*
Buck et al. (Biotechniques (1999) 27(3):528-536).*
GenBank: BC113568.1 (*Homo sapiens* phosphoglycerate kinase 1, mRNA, Jun. 29, 2006).*
Mensink et al. (British J. Haematol. (Aug. 1998) 102:768-774).*
De Lange, S.M. et al. 2004 "Phase II trial of cisplatin and gemcitabine in patients with advanced gastric cancer" *Annals of Oncology* 15(3): 484-488.
International Preliminary Report on Patentability for PCT Application No. PCT/EP2008/008322, dated May 11, 2010.
Kim, N.-S. et al. 2004 "Gene cataloging and expression profiling in human gastric cancer cells by expressed sequence tags" *Genomics* 83(6):1027-1045.
Krishnan, P. et al. 2002 "Phosphorylation of pyrimidine deoxynucleoside analog diphosphates: selective phosphorylation of L-nucleoside analog diphosphates by 3-phosphoglycerate kinase" *The Journal of Biological Chemistry* 277(7):5453-5459.
Rose, P. G. et al. 2003 "Gemcitabine reverses cisplatin resistance: Demonstration of activity in platinum-and multidrug-resistant ovarian and peritoneal carcinoma" *Gynecologic Oncology* 88(1): 17-21.
Sun, X.-M. et al. 2003 "Detection of type IV collagenase activity in malignant ascites" *World Journal of Gastroenterology* 9(11):2592-2595.
Wang, J. et al. 2007 "A glycolytic mechanism regulating an angiogenic switch in prostate cancer" *Cancer Research* 67(1):149-159.
Wang, L. et al. 2006 "Comparison of gene expression profiles between primary tumor and metastatic lesions in gastric cancer patients using laser microdissection and cDNA microarray" *World J. Gastroenterol* 12(43):6949-6954.

(Continued)

*Primary Examiner* — Peter J Reddig
(74) *Attorney, Agent, or Firm* — Knobbe, Martens, Olson & Bear, LLP

(57) ABSTRACT

The present invention relates to a method for diagnosing peritoneal carcinoses or metastatic primary tumors in a subject, as well as to a method for providing a prognosis to a subject diagnosed with a primary tumor to develop metastases, in particular peritoneal carcinosis, comprising the step of determining the level of expression of at least phosphoglycerate kinase 1 (PGK1) gene. Further, the invention relates to a diagnostic kit, comprising at least one substance for detection of the activity and/or expression of phosphoglycerate kinase 1 (PGK1) and/or β-catenin, either alone or in combination with the detection of CXCR4 and/or CXCL12, for the diagnosis or prognosis of peritoneal carcinoses and/or metastatic primary tumors. Also, a method for the preventive treatment of peritoneal carcinoses and/or metastatic primary tumors in a subject in need thereof is disclosed, wherein the method comprises the step of administering to the subject at least a pharmaceutically effective amount of a substance inhibiting the activity and/or expression of phosphoglycerate kinase 1 (PGK1).

7 Claims, 8 Drawing Sheets

(56) References Cited

OTHER PUBLICATIONS

Wolfram, M. 2003 "Reach-Through Claims" and "Reach-through licensing" *Mitteilungen der deutschen Paentanwälte* 94: 57-64.

Yasumoto, K. et al. 2006 "Role of the CXCL12/CXCR4 axis in peritoneal carcinomatosis of gastric cancer" *Cancer Res* 66(4):2181-2187.

Zhang, D. et al. 2005 "Proteomic study reveals that proteins involved in metabolic and detoxification pathyways are highly expressed in HER-2/neu-positive breast cancer" *Molecular & Cellular Proteomics* 4(11): 1686-1696.

Zieker, D. et al. 2008 "PGK1 a potential marker for peritoneal dissemination in gastric cancer" *Cellular Physiology and Biochemistry* 21: 429-436.

Kress, S. et al. 1998 "Expression of hypoxia-inducible genes in tumor cells" *J Cancer Res Clin Oncol* 124: 315-320.

\* cited by examiner

1 MSLSNKLTLD KLDVKGKRVV MRVDFNVPMK NNQITNNQRI KAAVPSIKFC LDNGAKSVVL
61 MSHLGRPDGV PMPDKYSLEP VAVELKSLLG KDVLFLKDCV GPEVEKACAN PAAGSVILLE
121 NLRFHVEEEG KGKDASGNKV KAEPAKIEAF RASLSKLGDV YVNDAFGTAH RAHSSMVGVN
181 LPQKAGGFLM KKELNYFAKA LESPERPFLA ILGGAKVADK IQLINNMLDK VNEMIIGGGM
241 AFTFLKVLNN MEIGTSLFDE EGAKIVKDLM SKAEKNGVKI TLPVDFVTAD KFDENAKTGQ
301 ATVASGIPAG WMGLDCGPES SKKYAEAVTR AKQIVWNGPV GVFEWEAFAR GTKALMDEVV
361 KATSRGCITT IGGGDTATCC AKWNTEDKVS HVSTGGGASL ELLEGKVLPG VDALSNI

FIG. 2A

```
   1 agcgcacgtc ggcagtcggc tccctcgttg accgaatcac cgacctctct ccccagctgt
  61 atttccaaaa tgtcgctttc taacaagctg acgctggaca agctggacgt taaagggaag
 121 cgggtcgtta tgagagtcga cttcaatgtt cctatgaaga acaaccagat aacaaacaac
 181 cagaggatta aggctgctgt cccaagcatc aaattctgct tggacaatgg agccaagtcg
 241 gtagtcctta tgagccacct aggccggcct gatggtgtgc ccatgcctga caagtactcc
 301 ttagagccag ttgctgtaga actcaaatct ctgctgggca aggatgttct gttcttgaag
 361 gactgtgtag gcccagaagt ggagaaagcc tgtgccaacc cagctgctgg gtctgtcatc
 421 ctgctggaga acctccgctt tcatgtggag gaagaaggga agggaaaaga tgcttctggg
 481 aacaaggtta aagccgagcc agccaaaata gaagctttcc gagcttcact ttccaagcta
 541 ggggatgtct atgtcaatga tgcttttggc actgctcaca gagcccacag ctccatggta
 601 ggagtcaatc tgccacagaa ggctggtggg tttttgatga agaaggagct gaactacttt
 661 gcaaaggcct tggagagccc agagcgaccc ttcctggcca tcctgggcgg agctaaagtt
 721 gcagacaaga tccagctcat caataatatg ctggacaaag tcaatgagat gattattggt
 781 ggtggaatgg cttttacctt ccttaaggtg ctcaacaaca tggagattgg cacttctctg
 841 tttgatgaag agggagccaa gattgtcaaa gacctaatgt ccaaagctga gaagaatggt
 901 gtgaagatta ccttgcctgt tgactttgtc actgctgaca agtttgatga aatgccaag
 961 actggccaag ccactgtggc ttctggcata cctgctggct ggatgggctt ggactgtggt
1021 cctgaaagca gcaagaagta tgctgaggct gtcactcggg ctaagcagat tgtgtggaat
1081 ggtcctgtgg gggtatttga atgggaagct tttgcccggg gaaccaaagc tctcatggat
1141 gaggtggtga agccacttc tagggctgc atcaccatca taggtggtgg agacactgcc
1201 acttgctgtg ccaaatggaa cacggaggat aaagtcagcc atgtgagcac tggggtggt
1261 gccagttggg agctcctgga aggtaaagtc cttcctgggg tggatgctct cagcaatatt
1321 tagtactttc ctgccttta gttcctgtgc acagcccta agtcaactta gcattttctg
1381 catctccact tggcattagc taaaaccttc catgtcaaga ttcagctagt ggccaagaga
1441 tgcagtgcca ggaaccctta aacagttgca cagcatctca gctcatcttc actgcaccct
1501 ggatttgcat acattcttca agatcccatt tgaatttttt agtgactaaa ccattgtgca
1561 ttctagagtg catatattta tattttgcct gttaaaaga aagtgagcag tgttagctta
1621 gttctctttt gatgtaggtt attatgatta gctttgtcac tgtttcacta ctcagcatgg
1681 aaacaagatg aaattccatt tgtaggtagt gagacaaat tgatgatcca ttaagtaaac
1741 aataaaagtg tccattgaaa ccgtgatttt ttttttttc ctgtcatact ttgttaggaa
1801 gggtgagaat agaatcttga ggaacggatc agatgtctat attgctgaat gcaagaagtg
1861 gggcagcagc agtggagaga tgggacaatt agataaatgt ccattcttta tcaagggcct
1921 actttatggc agacattgtg ctagtgcttt tattctaact tttattttta tcagttacac
1981 atgatcataa tttaaaaagt caaggcttat aacaaaaaag ccccagccca ttcctcccat
2041 tcaagattcc cactccccag aggtgaccac tttcaactct tgagtttttc aggtatatac
2101 ctccatgttt ctaagtaata tgcttatatt gttcacttcc ttttttttta tttttaaag
2161 aaatctattt cataccatgg aggaaggctc tgttccacat atatttccac ttcttcattc
2221 tctcggtata gttttgtcac aattatagat tagatcaaaa gtctacataa ctaatacagc
2281 tgagctatgt agtatgctat gattaaattt acttatgtaa aaaaaaaaaa aaaaaaa
```

FIG. 2B

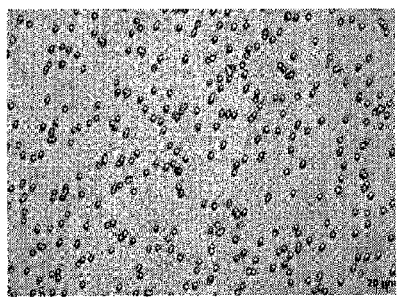 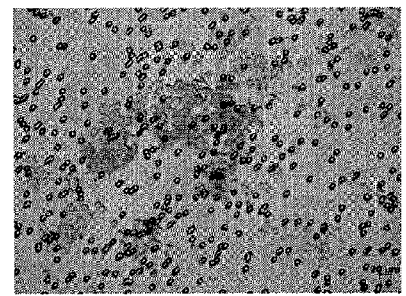
MKN 45 (non transfected)     MKN 45 (PGK1 transfected)
FIG. 6

MARKER FOR THE DIAGNOSIS OF CANCER

CROSS-REFERENCE TO RELATED APPLICATIONS

This application is a continuation of copending international patent application PCT/EP2008/008322, filed on Oct. 1, 2008, designating the U.S., which international patent application has been published in the German language and claims priority from German patent application DE 10 2007 048 636.9, filed on Oct. 2, 2007. The entire contents of these priority applications are incorporated herein by reference.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 8814285_1.txt, the date of creation of the ASCII text file is Apr. 2, 2010, and the size of the ASCII text file is 14.8 KB.

BACKGROUND OF THE INVENTION

1. Field of the Invention

The present invention generally concerns the use of markers for the diagnosis or prognosis of peritoneal carcinoses and/or metastatic primary tumors and methods for the detection or prognosis of such diseases in biological samples, use of the markers as targets for therapeutic treatment of these diseases, and relevant pharmaceutical compositions and diagnostic kits.

2. Description of the Related Art

Tumors generally constitute sites of tissue proliferation that occur as a result of pathologically excessive cell growth. Tumor cells, or cancer cells, are cells that are genetically altered—e.g., through mutations—and, because of unlimited division and the capacity to spread via the lymphatic vessels and blood vessels and thus to colonize other tissues, cause the formation of tumors.

Therefore, in addition to altered morphology, tumor cells are usually characterized by nuclear polymorphism and tend to form foci. This means that they are no longer inhibited from contact and can therefore form adhesions. Moreover, tumor cells frequently cease to function normally and often can no longer be detected because of dedifferentiation of their original tasks. In addition, the cell membranes of tumor cells show new, so-called tumor antigens or tumor-associated antigens that can be used as markers to diagnose tumors.

For example, the altered behavior of tumor cells and the presentation of tumor-associated antigens in the cell membrane are attributable to changes in gene expression and in the metabolism of the tumor cells, which also results in altered signal transduction. On the other hand, this altered behavioral pattern and expression pattern is associated with the occurrence of markers specific to the tumor cells, which can be used to detect the presence of tumors in the body of a patient.

Moreover, an important aspect of malignant tumors is the formation of metastases, also referred to as metastasis. In this process, tumor cells move from their primary location, which is referred to as the primary tumor, via blood or lymphatic vessels to organs and tissues showing no primary disease, where colonization of the cells occurs to form metastases, i.e. daughter tumors. This invasion allows tumors cells to spread throughout the body, and even to colonize tissues far removed from the primary tumor, in which new tumors can then be formed.

The occurrence of malignant tumors, i.e. carcinogenesis, can be divided into three phases: in the initial phase, the cell is irreversibly transformed, e.g. specifically via the activation of protooncogenes, via carcinogenic hormones, oncogenic viruses, genetic defects in the DNA repair system, mutations, acquired or congenital immune defects, radiation, or carcinogens. In the subsequent latent phase, the transformed cells proliferate through additional involvement of carcinogens or other factors, and in some cases, metastases may already form in this phase. Finally, in the manifestation phase of tumor formation, malignant forms that tend to grow in an infiltrative manner and form metastases develop from early forms or even from initially benign tumors.

Early detection and diagnosis of tumors, particularly metastatic tumors, is of vital importance so that treatments can be instituted as early and quickly as possible. The earlier the tumor is detected, the more favorable the prognosis for cure or successful treatment. At present, a number of tumor markers are in clinical use that, as mentioned above, constitute e.g. substances and or cellular changes whose qualitative and/or quantitative analysis can provide information on the presence, the course, or the prognosis of malignant tumors. As mentioned previously, such tumor markers may be membrane-bound tumor antigens, as well as receptors and cell markers that indicate the increased expression of oncogenes and monoclonal cell growth. Moreover, another possibility is provided by substances for tumor diagnosis that, compared to samples from healthy patients, can be found in elevated concentrations in tissue samples from diseased patients, e.g. in the serum, urine, and/or other body fluids, or in tissues. Such substances are synthesized and/or secreted by the tumor tissue, released by oncolysis, or form when the organism reacts to a tumor.

Types of tumors that usually have a fatal outcome include peritoneal carcinoses, which frequently develop in patients with gastric tumors, often following surgery. Peritoneal carcinoses are formed when cancer cells from gastric tumors disseminate throughout the abdominal cavity, i.e., these tumors are metastatic primary tumors. To date there is virtually no drug available for this type of tumor, making it an ominous disorder, particularly in view of the extremely low survival rate (5%) in patients with peritoneal carcinoses.

There is also no known marker available to date that would allow the prediction of primary tumor metastasis for many other metastatic primary tumors, particularly of the gastrointestinal tract. The gastrointestinal tract comprises the esophagus, stomach, small intestine, large intestine (colon), and pancreas, as well as the duodenum, jejunum, and ileum, which are the subdivisions of the small intestine. Tumors of the gastrointestinal tract are among the most common causes of cancer fatality in humans.

Using tumor markers, it is possible, for example, to conduct early examination of primary tumors in order to determine whether they are metastatic, which can allow early intervention, and in favorable cases, prevention of metastasis.

SUMMARY OF THE INVENTION

Therefore, an object of the present invention is to provide new markers for diagnosing metastatic primary tumors or for predicting a primary tumor to develop metastases, in particular in humans, and new therapy targets using such markers.

This object is achieved by providing a method for diagnosing peritoneal carcinoses and/or metastatic primary tumors in a subject, comprising steps of providing a sample of peritoneal tissue and/or primary tumor tissue obtained from the subject, and determining the level of expression of at least phosphoglycerate kinase 1 (PGK1) gene, or fragments thereof, thereby diagnosing the presence of peritoneal carcinoses or of metastatic primary tumors, particularly of the gastrointestinal tract, i.e. of primary tumors developing metastases, based on the expression levels in the provided tissue. In this case, PGK1 may be used either alone or, according to another aspect of the invention, in combination with β-catenin, CXCR4, and/or CXCL12 as markers.

According to another aspect, the invention concerns a method for the diagnosis of peritoneal carcinoses and/or metastatic primary tumors, in which overexpression of PGK1, either alone or in combination with β-catenin, CXCR4, and/or CXCL12, is used as a marker. The object is further achieved by means of a pharmaceutical composition containing at least one substance which inhibits the overexpression of PGK1 alone, or a combination with other substances that inhibit β-catenin, CXCR4, and/or CXCL12.

The object of the invention is fully achieved in this manner. By means of detailed comparative analyses between malignant tissue and non-malignant tissue, genes and proteins can be identified that differ significantly in the types of tissue in their frequency and/or concentration. The quantitative expression of a particular gene or protein in comparison with controls, particularly of the genes and proteins claimed in this application, thus constitutes an important indicator for the presence of tumor tissues, particularly metastatic primary tumors, which makes it possible to use these genes and/or proteins as diagnostic markers.

In experiments the inventions is based upon, the inventor discovered that said genes/proteins are particularly well-suited for use in metastatic primary tumors as markers for the diagnosis/prognosis of whether or not these tumors will form metastases, i.e. whether or not the primary tumor is metastatic or not.

In this regard, PGK1 can be used either alone as a marker for said tumor diseases, or in combination with one or more of the markers β-catenin, CXCR4, or CXCL12.

Phosphoglycerate kinase 1—referred to in the following, also, simply as "PGK1"—is an enzyme that catalyzes the reversible conversion of 3-phosphoglycerate to 1,3-diphosphoglycerate and ADP. The physiological significance of this enzyme lies mainly in the reverse reaction, by means of which the energy of the 1,3-diphosphoglycerate stored during glycolysis in the form of ATP is made available for energy-consuming metabolic reactions. The expression of PGK1 is regulated by hypoxia-inducible factor-1α (HIF-1α). The protein sequence of PGK1 is shown in FIG. 2A and designated with SEQ-ID No. 2 of the attached sequence listing, and the mRNA of PGK1 (see FIG. 2B) is designated with SEQ-ID No. 1.

PGK1 not only plays a role as a glycolytic enzyme, but also as a suppressor of proangiogenic factors such as VEGF (vascular endothelial cell growth factor) and interleukin IL-8. Apart from this, it is thought based on a more recent study that PGK1 is involved in the occurrence of malignant prostate tumors (cf. Wang et al., "A glycolytic mechanism regulating an angiogenic switch in prostate cancer," Cancer Research, 67: 149-159, 2007). Moreover, various research groups have observed overexpression of PGK1 in breast and pancreatic carcinomas and uterine cancer, but not yet in metastatic primary tumors of the gastrointestinal tract.

β-catenin, a 92 kD protein—in addition to its significance in cell adherens junctions and intercellular communication—also plays a vital role in signal transduction within the cell, cell proliferation, growth regulation, and embryonal development. β-catenin is involved in the formation of several proteins in healthy cells, and forms with these proteins transcription factors that stimulate cell proliferation and/or inhibition of cell death. β-catenin is also involved in the development of various forms of cancer, such as familial adenomatous polyposis, in which increased cell proliferation occurs due to functional incapacity of the tumor suppressor APC, which ordinarily binds excess β-catenin. In bowel cancer and some skin cancer lines, mutations are found in β-catenin itself that interfere with inactivation of 13-catenin by phosphorylation.

Nevertheless, there has not yet been a connection described between the expression of PGK1 and β-catenin in gastric cancer or in peritoneal dissemination of gastric cancer, i.e. in primary tumors of the gastrointestinal tract developing metastases.

Chemokines are secretory cytokines that can be classified into four groups based on structural differences, including the CXC group. Chemokine receptors show a particular structure, constituting G-protein-coupled receptors that cross the cell membrane with seven transmembrane α-helices. The known human chemokine system contains over 50 ligands and 20 G-protein-coupled receptors that regulate the migration and activation of leukocytes and affect angiogenesis and tumor growth. It is also thought based on prior art that tumor cells themselves can secrete chemokines. Disseminated tumor cells that express members of the CXCR family and enter the circulation are therefore intercepted by their corresponding ligands. This makes these cells capable of penetrating certain organs.

The chemokine receptor CXCR4, which is the receptor for the chemokine CXCL12, is expressed on various tumor cells, including cells in patients with chronic lymphocytic leukemia (CLL) and in primary tumors and cell lines of small cell lung carcinoma (SCLC). Moreover, it has now been discovered that chemokines can also promote the growth and metastasis of a number of malignant tumors. For this reason, the expression of chemokine receptors, particularly CXCR4, by tumor cells can constitute an important factor in organ-specific metastasis. For example, a role in metastasis was attributed to the interaction between CXCR4 and CXCL12 in breast and prostate cancer. Moreover, Yasumoto et al., in "Role of the CXCL12/CXCR4 Axis in Peritoneal Carcinomatosis of Gastric Cancer", Cancer Res. 66: 2181-2187 (2006), investigated the role of the CXCR4/CXCL12 interaction in peritoneal carcinoses in gastric cancer. In contrast, the finding that there is a connection between the expression of PGK1 and the expression of CXCR4/CXCL12 in peritoneal carcinoses in gastric cancer is new and has not yet been described in prior art.

Therefore, PGK1, either alone or in combination with β-catenin or CXCR4 and CXCL12, constitutes a suitable marker/marker combination for the diagnosis/prognosis of metastatic primary tumors and peritoneal carcinoses.

According to another aspect of the invention, the determining of the levels of expression of the genes comprises detecting either of the expression mRNA expressed form said genes or of the expression of polypeptides encoded by said genes.

In particular, upregulation of the PGK1-gene expression and/or PGK1 protein expression is determined, either alone or in combination with the upregulation of 13-catenin, CXCR4 and/or CXCL12, in comparison to gene/protein expression of PGK-1 in normal (i.e. non-malignant)/control tissue.

In the present case, "upregulation" or "increased expression" refers to any gene or protein expression of PGK1, CXCR4, CXCL12, and β-catenin that is increased or enhanced compared to normal expression of the gene in question in healthy samples. Comparison of the differing levels of expression may be carried out using controls or standards.

"Upregulated" or "increased" gene expression means that the gene in question is transcribed—in and if applicable, translated into the corresponding protein—to a greater extent than is normal for this gene, which may be attributable to various factors. It is therefore understood that the present invention comprises both, investigation of DNA sequences coding for PGK1, CXCR4, CXCL12, and β-catenin, as well as investigation of the frequency of the proteins themselves, or the RNA on which these proteins are based.

The protein sequence of the marker PGK1 is given in FIG. 2A, and the sequence of its mRNA is given in FIG. 2B of this Application. These sequences, as well as the gene sequence coding for PGK1, are listed in publicly available databases. For example, the mRNA of PGK1 is included in the database ("GenBank") of the National Center for Biotechnology Information (NCBI: http:/www.ncbi.nlm.nih.gov/) under Database No. NM_00291, the mRNA of CXCR4 under NM_003467, the mRNA of CXCL12 under NM_001033886, and the mRNA of β-catenin under NM_001904. The gene and protein sequences corresponding to the markers can also be identified via these mRNA database numbers, so the present invention expressly includes the respective sequences, or fragments thereof, published in the databases and used in the claimed methods.

Presently, as the term "marker" is used throughout the present application for both, the protein/gene product in question and the gene coding for this product, the term "marker" means a protein, gene product, and/or gene of PGK1, CXCR4, CXCL12, and 13-catenin.

The markers may be used, according to the invention, in analyses which may—with respect to gene expression—include the polymerase chain reaction (PCR), as well as gene chip/microarray systems, RNase protection assays, etc., and particularly any molecular biology method by which particular DNA or RNA sequences can be amplified. In this manner, one can carry out quantitative and qualitative detection of the gene products to be analyzed at the DNA or RNA level. In addition, however, detection may be carried out by means of hybridization tests using conventional northern or southern blots, by means of which quantitative/qualitative data on the quantity of proteins at the DNA or RNA level can be obtained.

Moreover, the markers can also be qualitatively and quantitatively determined at the protein level via conventional western blots, protein chips, using antibodies and/or immunoassays such as ELISA (enzyme-linked immunosorbent assay), immunohistochemical methods, etc.

According to another aspect of the invention, sequences, or fragments thereof, from the attached sequence list, specifically SEQ ID Nos. 3 through 8, 17 and 18, are employed in the claimed methods, for identifying the diagnostic markers for the prognosis or diagnosis of metastatic primary tumors.

The claimed sequences represent primers by means of which the respective gene products PGK1, CXCR4, CXCL12, and β-catenin can be identified, e.g. in quantitative real time PCR analysis. Thus, according to another aspect, the invention concerns a method which comprises the step of contacting the sample of a subject with or exposing mRNA expressed from said genes to a nucleic acid probe, which is selected from at least one of the sequences having SEQ ID Nos. 3 through 8, 17, and 18. It is understood that in the present invention, any other primer that can be used to identify the gene products PGK1, CXCR4, CXCL12, and β-catenin is also suitable for use according to the invention, so that the claimed primers can easily be modified, e.g. with respect to their length or common changes in the sequence, but still retain their function of detecting gene products.

Furthermore, the invention concerns a method for the prognosis or diagnosis of peritoneal carcinoses and/or metastatic primary tumors of the gastrointestinal tract, with said method comprising the, e.g. in vitro, detection of increased gene or protein expression of phosphoglycerate kinase 1 (PGK1) alone or in combination with increased gene or protein expression of CXCR4, CXCL12, and/or β-catenin in a biological sample.

With the method according to the invention, one can obtain reliable data on the likelihood of primary tumors to form metastases, as the markers according to the invention provide the appropriate tool for this task.

A particularly preferred embodiment of the method of the invention comprises the following steps:
a) Preparation of a biological sample of a human tumor patient to be examined,
b) Detection of increased gene and/or protein expression in the biological samples, compared to controls and/or standards, of at least one of the following genes or proteins: phosphoglycerate kinase 1 (PGK1), CXCR4, CXCL12, or β-catenin.

According to one aspect, the biological sample may be a fluid or solid body sample from a patient, specifically a sample of blood, serum, plasma, urine, tissue, bone, cartilage, organs, etc. This tissue sample may be a sample of a primary tumor, and the control may be either a sample of a non-metastatic tumor tissue or a standard. These samples may be taken and if necessary prepared according to methods known to a person skilled in the art.

As mentioned above, in the method according to the invention, detection/determination may be carried out using the auxiliary methods of polyacrylamide gel electrophoresis, immunohistochemistry, ELISA (enzyme-linked immunosorbent assay), gene/protein microarrays, PCR, etc. These methods are known in prior art, particularly in the area of medical research. Instructions for the use of these methods and other methods not discussed here may be found e.g. in Sambrook, Fritsch, and Maniatis, "Molecular Cloning, A Laboratory Manual", which is expressly referred to here.

The invention also concerns a diagnostic kit comprising at least one substance for detecting the activity and/or expression of phosphoglycerate kinase 1 (PGK1) alone or in combination with CXCR4, CXCL12, and/or β-catenin for the diagnosis and prognosis of metastatic primary tumors or peritoneal carcinoses.

This diagnostic kit can be advantageously used to determine the quantity of the markers according to the invention in biological samples, namely by comparing the gene/protein expression of the sample of interest that contains the marker or markers with controls or standards, specifically with respect to increased expression of the marker(s). The diagnostic kit is therefore particularly well-suited for the early detection of metastatic primary tumors, which in turn allows rapid and targeted therapy. Thus this diagnostic kit—as well as to claimed method—can also be used e.g. to distinguish between non-metastatic and metastatic gastric tumors. The diagnostic kit should preferably contain e.g. one or more antibodies or oligonucleotides that react with the marker/marker combinations according to the invention at the protein or gene level.

The invention also concerns the use of phosphoglycerate kinase 1 alone or in combination with CXCR4, CXCL12, and/or β-catenin as targets for the therapeutic or preventive treatment of metastatic primary tumors and peritoneal carcinoses.

According to yet another aspect, the invention also concerns a method for treatment and/or prevention of metastatic primary tumors and peritoneal carcinoses, the method comprising the step of administering to a subject in need thereof an effective amount of a substance that inhibits the activity and/or expression of phosphoglycerate kinase 1 (PGK1), either alone or in combination with a substance that inhibits the activity and/or expression of CXCR4, CXCL12, and/or β-catenin, and/or in combination with at least one chemo- or radiotherapeutic agent.

In addition to being suitable as diagnostic markers, the markers according to the invention are also suitable as targets for treatment with a substance that inhibits the activity and/or expression of the markers. As described above, the quantity of said markers in metastatic primary tumors is increased compared to non-metastatic primary tumors. Reducing the activity of expression of these markers to a comparatively normal activity/expression level therefore constitutes an approach for treating metastatic primary tumors that have been identified as such and/or an approach for preventing metastasis of the primary tumor.

The substance or active component with which the activity and/or expression of said markers can be inhibited represents, in particular, a specific antibody, which can advantageously be a blocking antibody or a radiolabeled antibody, with which so-called radioimmunotherapy can be conducted.

Several experiments on said proteins and/or genes showed that they were upregulated in tumor tissue in characteristic fashion compared to controls, i.e. they showed increased gene expression. According to the invention, therefore, corresponding active components or substances that cause downregulation of gene expression may be used in order to achieve a level of expression and/or activity of said genes/proteins comparable to that found in healthy tissues. On the other hand, active components/substances that e.g. act on the markers as blocking/inhibiting antibodies, thus inhibiting their activity, can also be used. The antibodies to be used are e.g. monoclonal antibodies, particularly recombinant humanized antibodies or chimeric antibodies. In addition to the variable region that imparts specificity against human antigens, conventional monoclonal antibodies also contain murine protein components; for this reason, the constant sections of the murine antibodies are removed by a molecular biology method and replaced by structurally identical constant portions of human antibodies.

The active components/substances used according to the invention may include, according to another aspect of the invention, peptides, proteins, so-called small molecular compounds, or polynucleotides, and they may be synthetic or natural active components. The substances may act either directly on the respective proteins or do so during gene expression. Short molecules may also be used, such as siRNAs (small interfering RNAs) and corresponding antisense oligonucleotides, such as antisense RNA or DNA, which can interfere with the corresponding genes and/or gene products and inhibit them.

The substances may also possess e.g. a blocking action, making it possible to use substances that possess e.g. receptor cells (such as CXCR4), thus interrupting the interaction between the receptor and its usual ligand(s).

The therapeutic agent that may be used together with a substance directed against PGK1 may be a chemo- and/or radiotherapeutic agent currently in common use for cancer therapy, such as radiolabeled, and particularly 125-labelled, active components, such as antibodies and naturally occurring substances (e.g. α-interferon, interleukin-12) or synthetically produced substances. Cytostatics having an antineoplastic effect may be used as chemotherapeutic agents. For example, quercetin, tamoxifen, or staurosporine, which are effective inhibitors of protein kinase C, are currently known as chemotherapeutic agents in cancer treatment. The substance group of the di-triazines, whose action is based on interaction with DNA, has also been developed.

Finally, according to another aspect, the present invention also concerns a pharmaceutical composition comprising a substance that inhibits the activity and/or expression of PGK1, either alone or in combination with an active component that inhibits the activity/expression of CXCR4, CXCL12, or β-catenin, optionally with at least one pharmaceutically acceptable carrier.

For example, the composition according to the invention may be administered systemically, such as by intravenous, oral, or subcutaneous administration, or locally, and the active components may be administered either together in a pharmaceutical composition, or separately in several compositions administered successively.

The composition may also include excipients commonly found in pharmaceutical compositions, and these may depend on the administration form, the patient, etc. A number of suitable substances are listed in A. Kibbe, Handbook of Pharmaceutical Excipients, 3. Ed., 2000, American Pharmaceutical Association and Pharmaceutical Press.

It is understood that the characteristics that are described above and will be further discussed below may be used not only in the respectively indicated combination, but also in other combinations or individually, without this preventing them from falling within the scope of the present invention.

BRIEF DESCRIPTION OF THE DRAWINGS

Further advantages can be taken from the following examples and the figures, which show the following:

FIG. 2: (A) Sequence of the PGK1 protein (SEQ ID NO: 2); and (B) the PGK1 mRNA (SEQ ID NO: 1).

FIG. 6 Analysis of the invasiveness of transfected and non-transfected cells: left: hundred-fold magnification: gastric carcinoma cells MKN45 without PGK1-overxpression;

Figure 1:
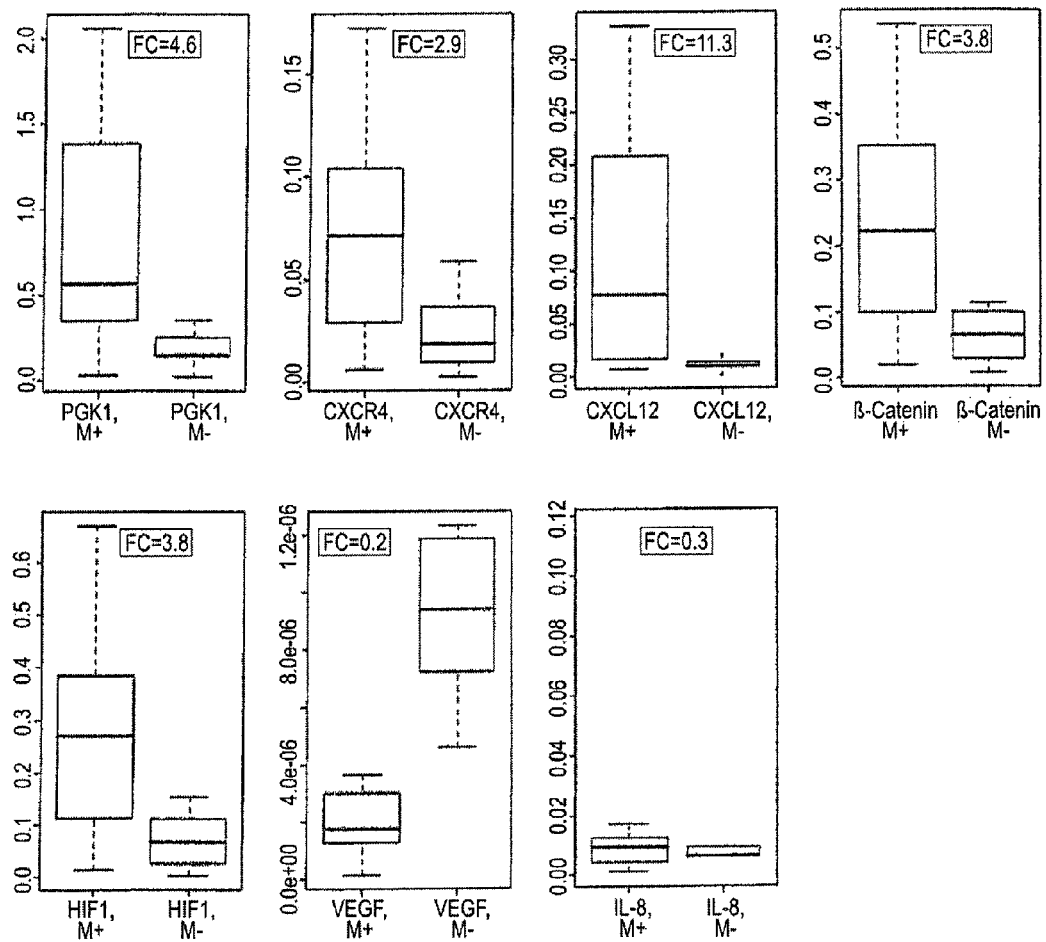
FIG. 1: Boxplots of quantitative real-time PCR measurements of RNA samples in individual patients. Each of the boxplots shows the respective minimum, quartile, mean value, tertile, and maximum for the distribution of the qRT-PCR values. For each gene, two boxplots were prepared, with the left ones indicating gastric tumor samples with peritoneal carcinoses (M+) and the right ones indicating samples without peritoneal carcinoses (M−); in addition, the mean value of the frequency change in the peritoneal carcinosis-positive samples with respect to the negative samples is shown for each gene.
Figure 3:
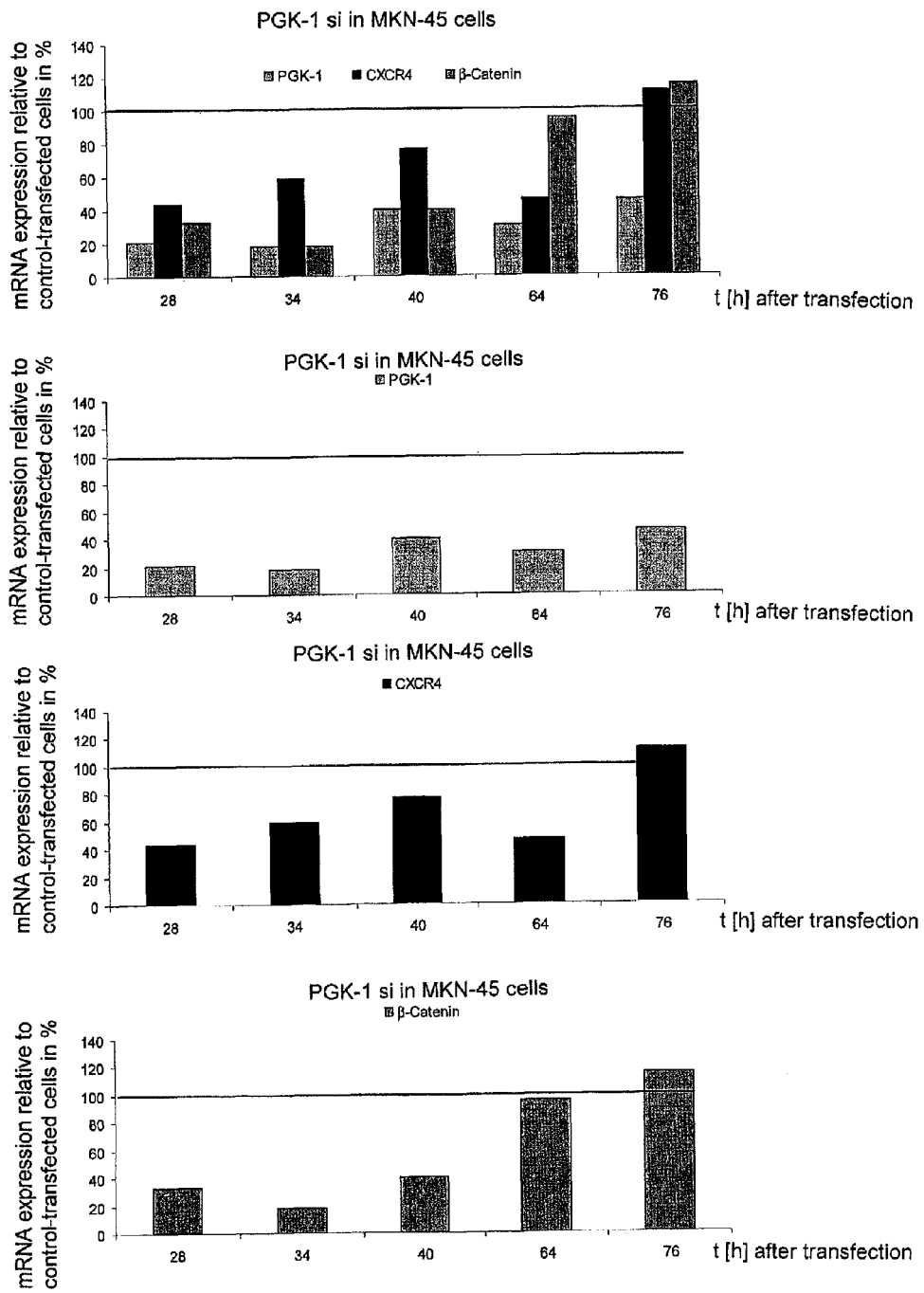
FIG. 3: Results of gene silencing experiments using siRNA on mRNA level: PGK1 influences the regulation of the signalling molecules CXCR4, CXCR12 and beta-Catenin and VEGF and vice versa.

right: hundred-fold magnification: gastric carcinoma cells MKN45 with PGK1-overexpression.

DETAILED DESCRIPTION OF THE PREFERRED EMBODIMENT

1. Materials and methods a: Patients, Tissue Samples, and RNA Extraction

Tissue samples from 13 patients (untreated, without any neoadjuvant therapy) with histologically confirmed diffuse gastric cancer who had undergone laparotomy were analyzed. In 8 of 13 patients, peritoneal carcinosis was histologically confirmed (5 female and 3 male patients; average age 58, age range 27-78). In 5 of 13 patients, no peritoneal carcinosis was confirmed (4 female and 1 male patient; average age 70, age range 60-76). All of the tumor samples were collected by the Department of General Surgery, GI Tract and Endocrine Surgery, and Transplantation Surgery, University of Tübingen, Germany. The samples were quick-frozen in liquid nitrogen and stored at −80° C. prior to use. Each tumor sample was cryosectioned, hematoxylin and eosin-stained, classified by two experienced pathologists, and then reevaluated by an experienced surgical pathologist. The RNA was extracted using the Nucleo Spin RNA II kit (Macherey-Nagel, Düren, Germany). RNA quality and quantity were confirmed using the Agilent 2100 Bioanalyzer (Agilent Technologies, Palo Alto, USA) and the NanoDrop Spectrophotometer (NanoDrop Technologies, Wilmington, Del., USA).

b: Microarray Data Generation

Microarray data were collected using oligonucleotide microarrays (65mer) manufactured at the Max Planck Institut, Tübingen, Germany. Each of the arrays contained oligonucleotides for approximately 900 transcripts, with each oligonucleotide being placed on the array twice. In this assay, primary tumor samples from patients with gastric cancer with and without the development of peritoneal carcinoses were compared (n=6; 3 patients who developed peritoneal carcinosis were compared to 3 patients who did not develop this disorder). In order to minimize variability because of the two dyes, 9 microarrays of 6 samples were conducted. Further details on the array may be obtained from the National Center for Biotechnology Information's Gene Expression Omnibus (on the World-Wide-Web at ncbi.nlm.nih.gov/geo/) under Access No. GPL5676. Amplification of the RNA samples was carried out using Ambion's Amino Allyl MessageAMP™ II RNA Amplification Kit (Ambion Inc., Austin, USA). Dye coupling reactions were carried out using the Amersham CyDye Postlabelling Reactive Dye Pack (GE Healthcare, Buckinghamshire, UK). After RNA fragmentation using Ambion fragmentation reagents, hybridization was carried out at 48° C. for 14 hours.

c: Quantitative Real Time PCR

The sample RNA was transcribed using the Transcriptor First Strand cDNA Synthesis Kit (Roche, Mannheim, Germany). Selected cDNAs were quantified by real time PCR on a LightCycler® Instrument (Roche, Mannheim, Germany). SYBR Green Jump Start TAQ ReadyMix (Sigma, Taufkirchen, Germany) was used according to the manufacturer's instructions for PCR-based amplification. The specificity of the PCR conditions was confirmed by determining the melting point and sequencing the product. Quantification of the level of gene expression was carried out by means of a benchmark run on an external standard curve together with the samples of interest. The primer sequences used are shown in Table 1.

d. Statistical Analysis

Raw data were collected using an ImaGene v. 5.0. Further statistical and bioinformatic analyses were carried out using the R language (www.r-project.org) and the Limma package of the Bioconductor Project (on the World-Wide-Web at bioconductor.org/). As the first step in signal extraction, the mean value of pixel distribution for each channel was used as the foreground signal, and the mean value for the background of each spot was used as an estimation value for the raw signal values. All of the spots were considered, regardless of their flag status. The test was carried out twice, with 9 arrays of 6 samples. The data were normalized by means of Loess normalization, specifically using expression values and corrected with respect to the Normexp background, followed by dye swap normalization and proportional normalization with respect to space arrays. Both the Loess and proportional normalization methods were used, as provided for in the Limma package. The log ratio M of the samples with peritoneal carcinosis vs. the samples without peritoneal carcinosis for each spot was recorded as the result on the computer. Based on the recorded M values, the differentially expressed genes were detected by using the Welch one-sample t test, as implemented in R.

e: Gene Silencing Experiments

Using gene silencing experiments the influence of PGK1 on the regulation of CXCR4/CXCL12/beta-Catenin/VEGF on the mRNA level and the protein level was determined. To this end, siRNA was used. The post-transcriptional gene silencing was performed with the lipid-based transcription reagent Lipofectamine RNAiMAX (Invitrogen, Pasiley, UK) according to the manufacturer's instructions in MKN-45 cells (gastric carcinoma cell line). The used siRNA (siGENOME ON-TARGETplus SMART-pool, Dharmacon, Chicago, USA) consisted of four different target siRNA's for one gene, in order to achieve a higher silencing efficiency. The sequences of the siRNA are shown in Table 4. As a control, MKN-45 cells were transfected simultaneously with control siRNA, which had no effect on the gene expression. The course of the changed gene expression was analyzed several times after transfection for the respective assays.

Gene expression on mRNA level was determined by qRT-PCR. RNA of the transfected cells was extracted using the RNeasy Mini Kit (Qiagen, Hilden, Germany) and subjected to qRT-PCR as described under c above. The primers used for the qRT-PCR are shown in Table 1.

The PGK1 protein expression was analyzed by western blot analysis. To this end, the transfected cells were lysed in RIPA buffer (Pierce, Rockford, USA) according to the instructions of the manufacturer and the whole proteins extracted. In the western blots, 50 µg of the whole protein of each sample was applied on a 10% polyacrylamide gel and separated according to their size via gel electrophoresis. The proteins ware blotted on a PVDF-membrane (Millipore, Billerica, USA). Apart from the primary antibodies for PGK1 (Abnova, Paipei, Taiwan), β-Actin (Affinity Bio Reagents, Golden, USA) was used as a control, also. The effects of PGK1 gene silencing on other proteins were analyzed by FACS.

The flow cytometric analysis of the harvested MKN45 cells was performed with each $5 \times 10^5$ cells with a vitality rate of at least 90% per assay. Intracellular staining was conducted with the Intra Prep permeabilization reagent (Beckman Coulter, Fullerton, USA) according to the manufacturer's instructions. A CXCR4 IgG2b antibody (R&D Minneapolis, USA) was used for the determination of protein expression, followed by labelling with a phycoerythrin conjugated secondary antibody (BD, Franklin Lakes, USA). Protein analysis of beta-Catenin was performed by using an Alexa 488 conjugated beta-Catenin antibody (Cell Signaling, Danvers, USA). For each antibody, a respective isotype control was used. After antibody incubation, the fluorochrome labelled and washed MKN-45 cells were analyzed in an Epics XL MCL Flow Cytometer (Beckman Coulter, Fullerton USA). Prior to the analysis, the correct working of the apparatus was assured by using Flow Check Beads Fluorospheres (Beckman Coulter, Fullerton, USA). Evaluation was performed by observing positive cells at the indicated excitation wavelength, taking into account the zero compensation of the nonspecific fluorescence signal using MKN-45 cells previously labelled with matching isotype control antibodies.

f: Overexpression

For PGK1 overexpression the gene was cloned in plasmid vector pEF-IRES. BY means of transfection reagent Tfx-50 (Promega, Madison, USA) the plasmid was transfected in MKN-45 cells according to the manufacturer's instructions. After 24 hr the transfected cells were cultivated in a selection medium (RPMI 1640, 20% FCS and 5 µg puromycin per ml). After one week, the cell selection was stopped and the positive clones stably overexpressing the plasmid vector and the resistance gene were persisting and were further cultivated. As soon as enough cells were on hand, whole RNA was isolated using the RNeasy Mni Kit (Qiagen, Hilden, Germany); according to c:, the mRNA expression of stably transfected MKN-45 pEF-IRES cells was compared with control-transfected cells. Gene expression on protein level was analyzed using western blots and FACS analyses, which were performed as previously described under e.

Invasiveness

PGK1 overexpressing MKN-cells were analyzed in view of their invasiveness compared to non-transfected cells using a gelatine loaded migration assay in a Boyden chamber.

Results

Figure 4A:
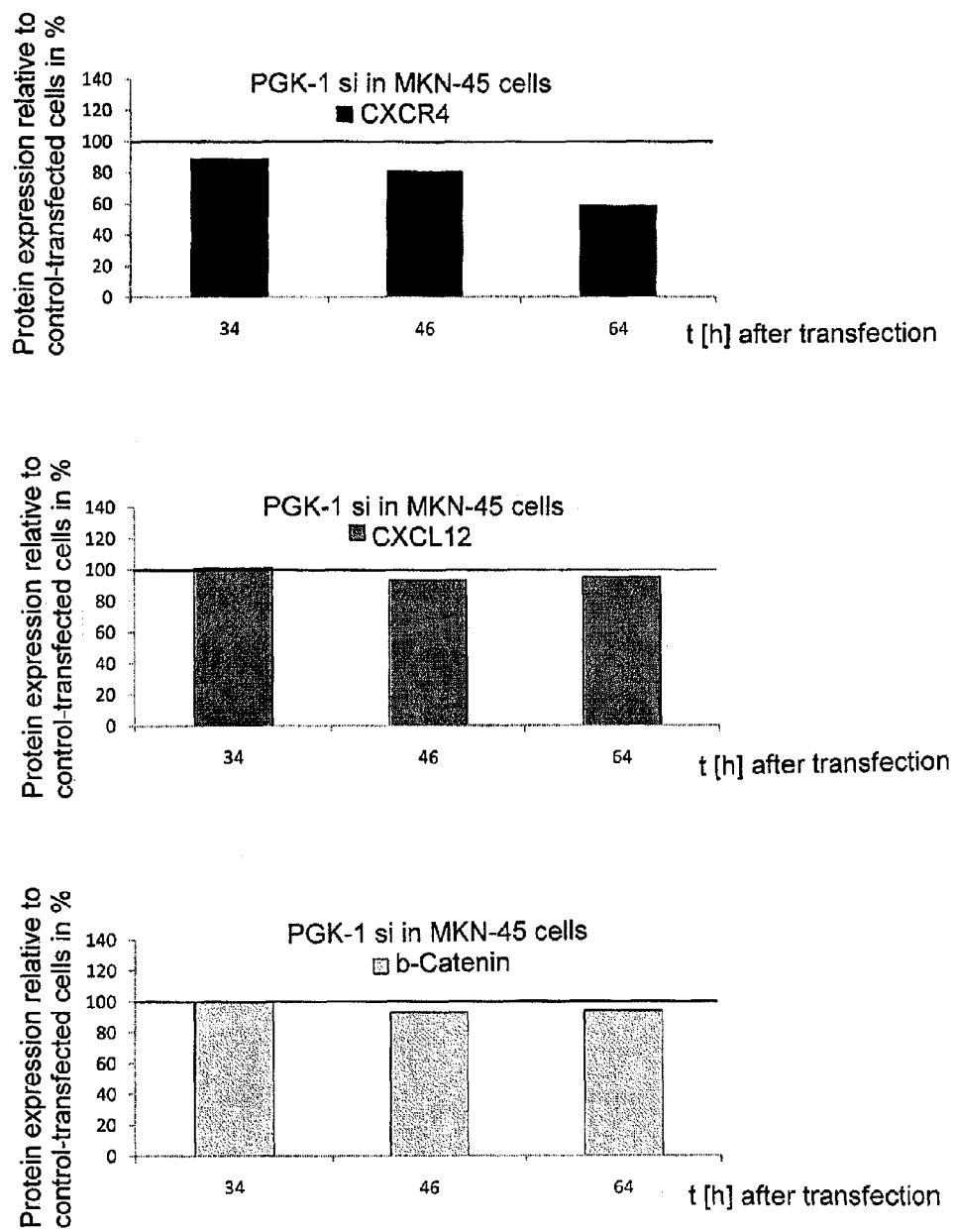
FIG. 4: Results of gene silencing experiments using siRNA on protein level; histograms (FIG. 4A) and western blots (FIG. 4B) are shown.
Figure 4B:
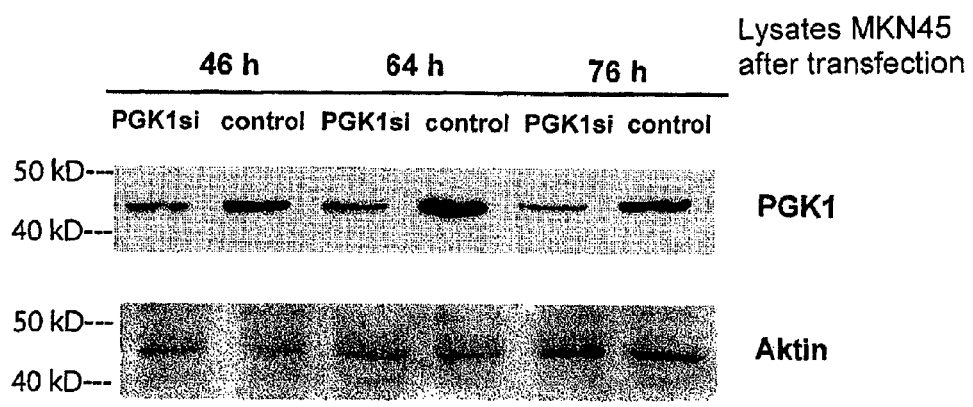

Gene expression analysis was carried out using a specially prepared oligomicroarrays. Several genes that were upregulated or downregulated compared to diffuse primary gastric tumor samples with and without peritoneal carcinoses were identified. After normalization, the t test was used to allow prognosis of differentially expressed genes in peritoneal carcinosis samples. At a level of significance of p<0.05, 57 genes were identified as showing differentiated regulation, of which 25 were upregulated in the peritoneal carcinosis samples and 32 were downregulated. In order to validate this result, 10 genes were selected for evaluation by quantitative real time PCR with pooled sample RNA. For all of these genes, the expression observed on the microarrays was confirmed, with the exception of E cadherin and S100. These results are shown in Table 2. A significant p value on the microarray and mRNA overexpression on real time PCR (pooled samples) were observed for PGK1 (p value=0.015) on the microarray, with a result of 5.2-fold in real time PCR in the primary tumor samples with known peritoneal carcinosis. Based on this result, additional genes were investigated using quantitative real time PCR on individual samples (not pooled). These genes were PGK1, HIF-1α, CXCR4, CXCL12, β-catenin, VEGF, and IL-8. Specific mRNA overexpression in diffuse primary tumors in stomach cancer with peritoneal carcinosis was detected for PGK1 (4.6-fold), HIF-1α(3.8-fold), CXCR4 (2.9-fold), CXCL12 (11.3-fold), and β-catenin (3.8-fold), while specific mRNA suppression of VEGF (5-fold) was detected in diffuse primary stomach cancer tumors with peritoneal carcinosis. For IL-8, a wide range of differences in expression was observed among the patients (see FIG. 4, outermost right plot in the bottom row). Nevertheless, both the array data and the quantitative real time PCR data from the pooled RNA indicated twofold downregulation in primary tumors of gastric cancer tissue with peritoneal carcinosis compared to primary tumors without peritoneal carcinosis. In a comparison of primary tumors with and without peritoneal carcinoses, no differences in cadherin mRNA were observed. The results of quantitative real time PCR for the individual samples are shown in Table 3.

Figure 5:
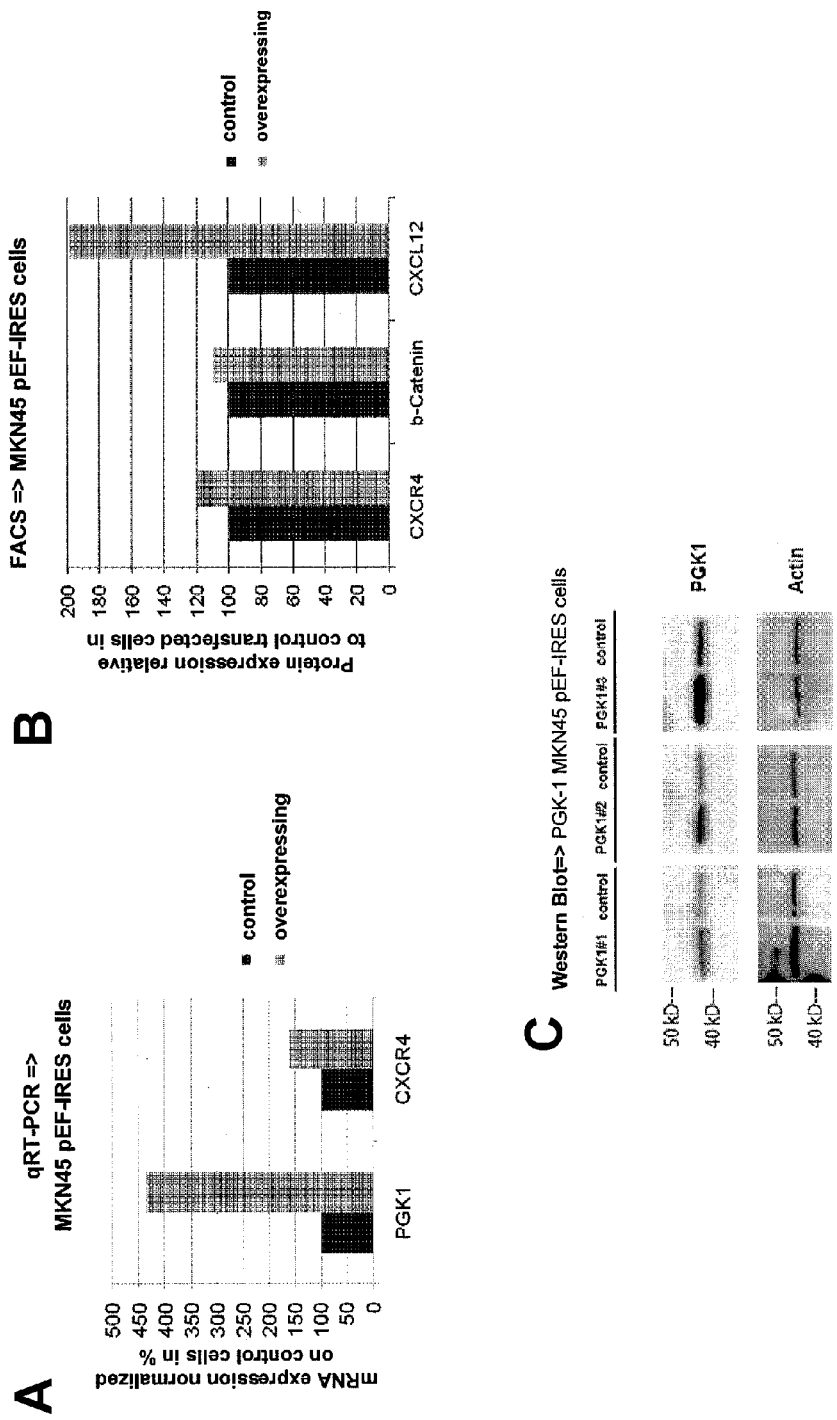
FIG. 5 Results of PGK1 overexpression (transfection of PGK1). (A) results on the level of gene expression using real-Time PCR of PGK1 and CXCR4. As can be seen, PGK1 mRNA and CXCR4 mRNA are upregulated compared to controls without transfection. (B) The results of CXCR4, β-Catenin and CXCL12 on protein level using FACS. As can be seen, these genes are, again, upregulated in the cells with PGK1-transfection as compared to the controls. (C) Proof that the PGK1 level is increased on protein level, also, in transfected cells compared to controls.

The gene silencing and overexpression experiments have shown that PGK1 has an important influence on the regulation of the signalling molecules CXCR4, CXCL12, beta-catenin and VEGF, and vice versa. These results confirm the data generated on expression level, so that the influence of PGK1 on its signalling molecules could be further confirmed and a regulation mechanism on expression and protein level could be shown (see FIG. 4a/b). The results of the PGK1 overexpression (transfection of PGK1) (see FIG. 5) show that PGK1 mRNA as well as CDCR4 mRNA was upregulated compared to controls without transfection (see FIG. 5A). Further, the FACS results of CXCR4, β-Catenin and CXCL12 on protein level show that these genes are upregulated in the cells with PGK1 transfection, again, compared to controls (see FIG. 5B). Also, it could be shown, that PGK1 is increased on protein level in the transfected cells, also, compared to the controls (see FIG. 5C).

The analyses regarding the invasiveness of the cells with and without PGK1 overexpression showed that from the gastric carcinoma cells MKN45 without PGK1 overexpression only two cells invaded the gel (see FIG. 6, right).

This fiftyfold increased invasiveness of gastric carcinoma cells mediated by a PGK1-overexpression compared to gastric carcinoma cells without PGK1-overexpression shows the malignancy increasing influence of PGK1 and its signalling molecules in view of tumorgenesis and peritoneal carcinosis.

Discussion

In the tests described above, the differential expression of genes in samples from patients with diffuse gastric cancer with and without peritoneal carcinoses were investigated using oligonucleotide microarrays and quantitative real time PCR. In the view of the applicant, this constitutes the first study that shows highly specific overexpression of PGK1 mRNA in diffuse primary gastric cancer with histologically confirmed peritoneal carcinosis.

In addition to its function as a glycolytic enzyme, PGK1 has also been shown to play an important role in malignant tumors such as breast cancer, uterine cancer, and pancreatic cancer, but not yet in gastric cancer. The results of this study show that PGK1 overexpression could promote dissemination in the peritoneum.

It is well-known that HIF-1α regulates the expression of PGK1. The elimination of HIF-1α stops the induction of PGK1, which confirms that PGK1 is a downstream target of HIF-1α. These results show overexpression of HIF-1α mRNA in primary gastric cancer tumors with peritoneal carcinoses, a finding that shows a clear relation with the PGK1 expression values obtained.

These results also showed a significant increase in CXCR4 and CXCL12 mRNA, as well as strong suppression of VEGF and IL-8 mRNA in gastric cancer tissue with peritoneal carcinoses. Accordingly, these results are also the first to show a strong link between PGK1 regulation and the CXCR4-/CXCL12 axis in diffuse primary gastric cancer with known peritoneal carcinoses.

The present results also showed overexpression of β-catenin mRNA in primary tumors with peritoneal carcinosis. These results are not consistent with reports in which prostate cancer cell lines were investigated and in which high levels of PGK1 lead to downregulated expression of β-catenin.

To date there are no true diagnosis markers available that would allow prognosis of whether a primary gastric tumor will spread into the peritoneum. Although there are a few quantitative prognosis markers that serve as guidelines in selecting treatment in order to achieve the maximum therapeutic effect, these cannot be used to predict whether spreading will occur.

The highly clear differential expression of PGK1, HIF-1α, CXCR4, CXCL12, β-catenin, and VEGF is highly specific. For this reason, these molecules may be used as outstanding markers, either individually or in combination, in order to detect primary tumors that are highly likely to spread into the peritoneum and to develop metastases.

TABLE 2

An overview of differentially regulated genes from the microarray assays, which were evaluated with pooled RNA samples used in quantitative real time PCR (qRT-PCR) taken from the same patients as the samples used in the microarray tests. The indicated changes in frequency refer to genes that are specific for diffuse primary tumors in gastric cancer with peritoneal carcinoses.

| Gene Product | Accession Number | qRT-PCR-fold change | Array-fold change |
| --- | --- | --- | --- |
| E-Cadherin | NM_04360 | unchanged | 0.5 |
| CDK8 | NM_001260 | 1.49 | 1.9 |
| HIF1A | NM_01530 | 5.43 | 1.68 |

TABLE 1

Listing of primer sequences (human) for the quantitative real-time PCR analysis.

| Gene Product | Sense Primer | SEQ ID NO | Antisense Primer | SEQ ID NO |
| --- | --- | --- | --- | --- |
| Phosphoglycerate Kinase 1 (PGK1) | CATACCTGCTGGCTGGATGG | 3 | CCCACAGGACCATTCCACAC | 4 |
| Chemokine receptor 4 (CXCR4) | CAGTTTCAGCACATCATGGTTGG | 5 | GTGACAGCTTGGAGATGATAATGC | 6 |
| Chemokine receptor 12 (CXCL12) | GTCAAGCATCTCAAAATTCTCACCAC | 7 | CACTTTAGCTTCGGGTCAATGC | 8 |
| Hypoxia-inducible factor 1, alpha (HIF1A) | CAACCTCAGTGTGGGTATAAGAAAC | 9 | AAATTTCATATCCAGGCTGTGTCG | 10 |
| Vascular endothelial growth factor (VEGF) | GCCTTCGCTTACTCTCAC | 11 | GCTGCTTCTTCCAACAATG | 12 |
| Interleukin 8 (IL-8) | TCCATAAGGCACAAACTTTCAGAG | 13 | AATCAGGAAGGCTGCCAAGAG | 14 |
| Cadherin 1 (CDH1) | TGATGTGAACACCTACAATGC | 15 | CTCCTGTGTTCCTGTTAATGG | 16 |
| Catenin, beta 1 (CTNNB1) | GTCTTACCTGGACTCTGGAATCC | 17 | GGTATCCACATCCTCTTCCTCAG | 18 |
| Cyclin-dependent kinase 8 (CDK8) | GACCCACTTCCTACATCAGACG | 19 | CTTTGTCATCAGGTTCTTCTTCCG | 20 |
| Heat shock 70 Protein 1A (HSPA1A) | TCGAGAGTGACTCCCGTTGTC | 21 | GGCTGGAAACGGAACACTGG | 22 |
| Interleukin 1, beta (IL-1B) | TGGCCCTAAACAGATGAAGTGC | 23 | GTAGTGGTGGTCGGAGATTCG | 24 |
| Tumor protein p53 (TP53) | GGGACGGAACAGCTTTGAGG | 25 | TTCTTGCGGAGATTCTCTTCCTC | 26 |
| S100 Calcium binding protein A8 (S100A8) | AAGCCTTGAACTCTATCATCG | 27 | ACTCGGTCTCTAGCAATTTC | 28 |
| Sphingosine-1-phosphate phosphotase 2 (SGPP2) | GTATTATACTCATGGTTCAAGGTG | 29 | GTGTAGGTAACAAACTTGTAAGG | 30 |

TABLE 2-continued

An overview of differentially regulated genes from the microarray assays, which were evaluated with pooled RNA samples used in quantitative real time PCR (qRT-PCR) taken from the same patients as the samples used in the microarray tests. The indicated changes in frequency refer to genes that are specific for diffuse primary tumors in gastric cancer with peritoneal carcinoses.

| Gene Product | Accession Number | qRT-PCR-fold change | Array-fold change |
|---|---|---|---|
| PGK1 | NM_00291 | 5.2 | 1.19 |
| IL-1beta | NM_00575 | 0.27 | 0.86 |
| IL-8 | NM_000634 | 0.51 | 0.62 |
| p53 | NM_000546 | 3.58 | 1.04 |
| S100 | NM_002964 | unchanged | 0.53 |
| HSP70 | NM_005345 | 2.01 | 2.99 |
| SGPP2 | NM_152386 | 0.61 | 0.32 |

TABLE 3

Summary of a test in which selected genes were evaluated by means of quantitative real-time PCR (qRT-PCR) of individual samples. The indicated changes in frequency refer to differentially regulated genes that are specific for diffuse primary tumors in gastric cancer with peritoneal carcinoses.

| Gene Product | Accession Number | pRT-PCT- fold change |
|---|---|---|
| PGK1 | NM_000291 | 4.6 |
| HIF1A | NM_001530 | 3.8 |
| CXCR4 | NM_003467 | 2.9 |
| CXCL12 | NM_001033886 | 11.3 |
| VEGF | NM_003376 | 0.2 |
| IL-8 | NM_000584 | 0.3 |
| β-Catenin | NM_001904 | 3.8 |
| Cadherin | NM_004360 | unchanged |

TABLE 4

Sequences of the siRNA's used in gene silencing experiments.
siGENOME ON-TARGETplus SMARTpool

| | Sense Sequence | SEQ ID NO | Antisense Sequence | SEQ ID NO |
|---|---|---|---|---|
| PGK1 duplex (6) | GGACAAGCUGGACGUUAAAUU | 31 | 5'-P-UUUAACGUCCAGCUUGUCCUU | 32 |
| PGK1 duplex (7) | GGGCGGACGUAAAGUUGCAUU | 33 | 5'-P-UGCAACUUUAGCUCCGCCCUU | 34 |
| PGK1 duplex (8) | GAACAAGGUUAAAGCCGAGUU | 35 | 5'-P-CUCGGCUUUAACCUUGUUCUU | 36 |
| PGK1 duplex (9) | GAGCUGAACUACUUUGCAAUU | 37 | 5'-P-UUGCAAAGUAGUUCAGCUCUU | 38 |
| CXCR4 duplex (6) | GAAGCAUGACGGACAAGUAUU | 39 | 5'-P-UACUUGUCCGUCAUGCUUCUU | 40 |
| CXCR4 duplex (7) | GGCCUUAUCCUGCCUGGUAUU | 41 | 5'-P-UACCAGGCAGGAUAAGGCCUU | 42 |
| CXCR4 duplex (8) | UAACUACACCGAGGAAAUGUU | 43 | 5'-P-CAUUUCCUCGGUGUAGUUAUU | 44 |
| CXCR4 duplex (9) | CAAGCAAGGGUGUGAGUUUUU | 45 | 5'-P-AAACUCACACCCUUGCUUGUU | 46 |

What is claimed is:

1. A method for diagnosing a peritoneal carcinosis formed from a cancer cell from a gastric tumor that has disseminated to the abdominal cavity in a subject, comprising steps of:
   (a) providing a peritoneal tumor sample from the subject;
   (b) determining the level of expression in the peritoneal tumor sample of the phosphoglycerate kinase 1 (PGK1) gene, wherein the determining comprises
      analysis of PGK 1 gene expression through an assay selected from the group consisting of amplification of DNA or RNA, gene chip/microarray systems, RNase protection assays, and hybridization tests, wherein the assay comprises exposing mRNA expressed from said PGK1 gene to a nucleic acid probe consisting of at least one of the sequences having SEQ ID Nos. 3 and/or 4;
   (c) comparing the level of expression of the PGK1 gene in the peritoneal tumor sample to a level of expression of the PGK1 gene in a corresponding, non-malignant biological sample; and
   (d) diagnosing the peritoneal carcinosis as being formed from a cancer cell from a gastric tumor that has disseminated to the abdominal cavity based on a statistically significant overexpression of the PGK1 gene in the provided peritoneal tumor sample compared to the non-malignant biological sample.

2. The method of claim 1, wherein the step of determining the level of expression comprises determining the level of a set of genes comprising PGK1 and at least one or more genes selected from the group consisting of β-catenin, CXCR4, and CXCL12.

3. The method of claim 1, wherein upregulation of phosphoglycerate kinase 1 (PGK1), CXCR4, CXCL12, and/or β-catenin mRNA expression is investigated.

4. A method for providing to a subject diagnosed with a primary gastric tumor a prognosis of likelihood to develop peritoneal metastases or other metastases of the primary gastric tumor, said method comprising steps of:
   (a) providing a sample of primary gastric tumor tissue obtained from the subject;
   (b) determining the level of expression in the primary gastric tumor tissue of the phosphoglycerate kinase 1 (PGK1) gene to obtain a gene expression pattern for the sample, wherein the determining comprises:
      analysis of PGK 1 gene expression through an assay selected from the group consisting of amplification of DNA or RNA, gene chip/microarray systems, RNase protection assays, and hybridization tests, wherein the assay comprises exposing mRNA expressed from said PGK1 gene to a nucleic acid probe consisting of at least one of the sequences having SEQ ID Nos. 3 and/or 4;
   (c) comparing the level of expression of the PGK1 gene in the primary gastric tumor tissue to a level of expression of the PGK1 gene in a corresponding, non-malignant biological sample; and (d) providing the prognosis of likelihood to develop peritoneal metastases or other metastases of the primary gastric tumor to the subject based on a statistically significant overexpression level of the PGK1 gene in the provided sample of primary gastric tumor tissue compared to the non-malignant biological sample.

5. The method of claim 4, wherein the step of determining the level of expression comprises determining the level of a set of genes comprising PGK1 and at least one or more genes selected from the group consisting of β-catenin, CXCR4, and CXCL12.

6. The method of claim 1, further comprising:
(e) directing the subject to obtain treatment for the peritoneal carcinosis when the peritoneal carcinosis is diagnosed as being formed from a cancer cell from a gastric tumor that disseminated to the abdominal cavity.

7. The method of claim 4, further comprising:
(c) directing the subject to obtain treatment to lessen the likelihood of peritoneal metastasis or other metastasis of the primary gastric tumor when the prognosis is provided.

* * * * *

SEQUENCE LISTING

<160> NUMBER OF SEQ ID NOS: 46

<210> SEQ ID NO 1
<211> LENGTH: 2338
<212> TYPE: DNA
<213> ORGANISM: Homo sapiens

<400> SEQUENCE: 1

```
agcgcacgtc ggcagtcggc tccctcgttg accgaatcac cgacctctct ccccagctgt      60
atttccaaaa tgtcgctttc taacaagctg acgctggaca gctggacgt taagggaag       120 cgggtcgtta tgagagtcga cttcaatgtt cctatgaaga caaccagat aacaaacaac      180 cagaggatta aggctgctgt cccaagcatc aaattctgct tggacaatgg agccaagtcg     240
gtagtcctta tgagccacct aggccggcct gatggtgtgc ccatgcctga caagtactcc     300
ttagagccag ttgctgtaga actcaaatct ctgctgggca aggatgttct gttcttgaag     360
gactgtgtag gcccagaagt ggagaaagcc tgtgccaacc cagctgctgg gtctgtcatc     420
ctgctggaga acctccgctt tcatgtggag gaagaaggga agggaaaaga tgcttctggg     480
aacaaggtta aagccgagcc agccaaaata gaagctttcc gagcttcact ttccaagcta     540
ggggatgtct atgtcaatga tgcttttggc actgctcaca gagcccacag ctccatggta     600
```

-continued

```
ggagtcaatc tgccacagaa ggctggtggg tttttgatga agaaggagct gaactacttt      660
gcaaaggcct tggagagccc agagcgaccc ttcctggcca tcctgggcgg agctaaagtt      720
gcagacaaga tccagctcat caataatatg ctggacaaag tcaatgagat gattattggt      780
ggtggaatgg cttttacctt ccttaaggtg ctcaacaaca tggagattgg cacttctctg      840
tttgatgaag agggagccaa gattgtcaaa gacctaatgt ccaaagctga agaatggt        900
gtgaagatta ccttgcctgt tgactttgtc actgctgaca agtttgatga gaatgccaag      960
actggccaag ccactgtggc ttctggcata cctgctggct ggatgggctt ggactgtggt     1020
cctgaaagca gcaagaagta tgctgaggct gtcactcggg ctaagcagat tgtgtggaat     1080
ggtcctgtgg gggtatttga atgggaagct tttgcccggg aaccaaagc tctcatggat      1140
gaggtggtga agccacttc tagggcctgc atcaccatca taggtggtgg agacactgcc     1200
acttgctgtg ccaaatggaa cacggaggat aaagtcagcc atgtgagcac tggggtggt     1260
gccagtttgg agctcctgga aggtaaagtc cttcctgggg tggatgctct cagcaatatt     1320
tagtactttc ctgccttta gttcctgtgc acagcccta agtcaactta gcattttctg      1380
catctccact tggcattagc taaaaccttc catgtcaaga ttcagctagt ggccaagaga     1440
tgcagtgcca ggaacccta acagttgca cagcatctca gctcatcttc actgcaccct      1500
ggatttgcat acattcttca agatcccatt tgaattttt agtgactaaa ccattgtgca     1560
ttctagagtg catatattta tattttgcct gttaaaaga aagtgagcag tgttagctta     1620
gttctctttt gatgtaggtt attatgatta gctttgtcac tgtttcacta ctcagcatgg    1680
aaacaagatg aaattccatt tgtaggtagt gagacaaat tgatgatcca ttaagtaaac     1740
aataaaagtg tccattgaaa ccgtgatttt tttttttc ctgtcatact tgttaggaa       1800
gggtgagaat agaatcttga ggaacggatc agatgtctat attgctgaat gcaagaagtg    1860
gggcagcagc agtggagaga tgggacaatt agataaatgt ccattcttta tcaagggcct    1920
actttatggc agacattgtg ctagtgcttt tattctaact tttatttta tcagttacac    1980
atgatcataa tttaaaaagt caaggcttat aacaaaaaag ccccagccca ttcctcccat    2040
tcaagattcc cactccccag aggtgaccac tttcaactct tgagtttttc aggtatatac    2100
ctccatgttt ctaagtaata tgcttatatt gttcacttcc tttttttta tttttaaag     2160
aaatctattt cataccatgg aggaaggctc tgttccacat atatttccac ttcttcattc    2220
tctcggtata gttttgtcac aattatagat tagatcaaaa gtctacataa ctaatacagc    2280
tgagctatgt agtatgctat gattaaattt acttatgtaa aaaaaaaaa aaaaaaa        2338
```

<210> SEQ ID NO 2
<211> LENGTH: 417
<212> TYPE: PRT
<213> ORGANISM: Homo sapiens

<400> SEQUENCE: 2

```
Met Ser Leu Ser Asn Lys Leu Thr Leu Asp Lys Leu Asp Val Lys Gly
1               5                   10                  15

Lys Arg Val Val Met Arg Val Asp Phe Asn Val Pro Met Lys Asn Asn
            20                  25                  30

Gln Ile Thr Asn Asn Gln Arg Ile Lys Ala Ala Val Pro Ser Ile Lys
        35                  40                  45

Phe Cys Leu Asp Asn Gly Ala Lys Ser Val Val Leu Met Ser His Leu
    50                  55                  60
```

-continued

Gly Arg Pro Asp Gly Val Pro Met Pro Asp Lys Tyr Ser Leu Glu Pro
65                  70                  75                  80

Val Ala Val Glu Leu Lys Ser Leu Leu Gly Lys Asp Val Leu Phe Leu
            85                  90                  95

Lys Asp Cys Val Gly Pro Glu Val Glu Lys Ala Cys Ala Asn Pro Ala
            100                 105                 110

Ala Gly Ser Val Ile Leu Leu Glu Asn Leu Arg Phe His Val Glu Glu
            115                 120                 125

Glu Gly Lys Gly Lys Asp Ala Ser Gly Asn Lys Val Lys Ala Glu Pro
            130                 135                 140

Ala Lys Ile Glu Ala Phe Arg Ala Ser Leu Ser Lys Leu Gly Asp Val
145                 150                 155                 160

Tyr Val Asn Asp Ala Phe Gly Thr Ala His Arg Ala His Ser Ser Met
            165                 170                 175

Val Gly Val Asn Leu Pro Gln Lys Ala Gly Phe Leu Met Lys Lys
            180                 185                 190

Glu Leu Asn Tyr Phe Ala Lys Ala Leu Glu Ser Pro Glu Arg Pro Phe
            195                 200                 205

Leu Ala Ile Leu Gly Gly Ala Lys Val Ala Asp Lys Ile Gln Leu Ile
210                 215                 220

Asn Asn Met Leu Asp Lys Val Asn Glu Met Ile Ile Gly Gly Gly Met
225                 230                 235                 240

Ala Phe Thr Phe Leu Lys Val Leu Asn Asn Met Glu Ile Gly Thr Ser
            245                 250                 255

Leu Phe Asp Glu Glu Gly Ala Lys Ile Val Lys Asp Leu Met Ser Lys
            260                 265                 270

Ala Glu Lys Asn Gly Val Lys Ile Thr Leu Pro Val Asp Phe Val Thr
            275                 280                 285

Ala Asp Lys Phe Asp Glu Asn Ala Lys Thr Gly Gln Ala Thr Val Ala
            290                 295                 300

Ser Gly Ile Pro Ala Gly Trp Met Gly Leu Asp Cys Gly Pro Glu Ser
305                 310                 315                 320

Ser Lys Lys Tyr Ala Glu Ala Val Thr Arg Ala Lys Gln Ile Val Trp
            325                 330                 335

Asn Gly Pro Val Gly Val Phe Glu Trp Glu Ala Phe Ala Arg Gly Thr
            340                 345                 350

Lys Ala Leu Met Asp Glu Val Val Lys Ala Thr Ser Arg Gly Cys Ile
            355                 360                 365

Thr Thr Ile Gly Gly Gly Asp Thr Ala Thr Cys Cys Ala Lys Trp Asn
370                 375                 380

Thr Glu Asp Lys Val Ser His Val Ser Thr Gly Gly Gly Ala Ser Leu
385                 390                 395                 400

Glu Leu Leu Glu Gly Lys Val Leu Pro Gly Val Asp Ala Leu Ser Asn
            405                 410                 415

Ile

<210> SEQ ID NO 3
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 3
catacctgct ggctggatgg                                          20

```
<210> SEQ ID NO 4
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 4
cccacaggac cattccacac                                                    20

<210> SEQ ID NO 5
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 5
cagtttcagc acatcatggt tgg                                                23

<210> SEQ ID NO 6
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 6
gtgacagctt ggagatgata atgc                                               24

<210> SEQ ID NO 7
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 7
gtcaagcatc tcaaaattct caacac                                             26

<210> SEQ ID NO 8
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 8
cactttagct tcgggtcaat gc                                                 22

<210> SEQ ID NO 9
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 9
caacctcagt gtgggtataa gaaac                                              25

<210> SEQ ID NO 10
<211> LENGTH: 24
<212> TYPE: DNA
<213> ORGANISM: Artificial Sequence
<220> FEATURE:
```

-continued

<223> OTHER INFORMATION: oligonucleotide primer

<400> SEQUENCE: 10
aaatttcata tccaggctgt gtcg                                            24

<210> SEQ ID NO 11
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 11
gccttcgctt actctcac                                                   18

<210> SEQ ID NO 12
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 12
gctgcttctt ccaacaatg                                                  19

<210> SEQ ID NO 13
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 13
tccataaggc acaaactttc agag                                            24

<210> SEQ ID NO 14
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 14
aatcaggaag gctgccaaga g                                               21

<210> SEQ ID NO 15
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 15
tgatgtgaac acctacaatg c                                               21

<210> SEQ ID NO 16
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 16
ctcctgtgtt cctgttaatg g                                               21

```
<210> SEQ ID NO 17
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 17
gtcttacctg gactctggaa tcc                                              23

<210> SEQ ID NO 18
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 18
ggtatccaca tcctcttcct cag                                              23

<210> SEQ ID NO 19
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 19
gacccacttc ctacatcaga cg                                               22

<210> SEQ ID NO 20
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 20
ctttgtcatc aggttcttct tccg                                             24

<210> SEQ ID NO 21
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 21
tcgagagtga ctcccgttgt c                                                21

<210> SEQ ID NO 22
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 22
ggctggaaac ggaacactgg                                                  20

<210> SEQ ID NO 23
<211> LENGTH: 22
<212> TYPE: DNA
<213> ORGANISM: Artificial Sequence
<220> FEATURE:
<223> OTHER INFORMATION: oligonucleotide primer
```

```
<400> SEQUENCE: 23
tggccctaaa cagatgaagt gc                                              22

<210> SEQ ID NO 24
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 24
gtagtggtgg tcggagattc g                                               21

<210> SEQ ID NO 25
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 25
gggacggaac agctttgagg                                                 20

<210> SEQ ID NO 26
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 26
ttcttgcgga gattctcttc ctc                                             23

<210> SEQ ID NO 27
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 27
aagccttgaa ctctatcatc g                                               21

<210> SEQ ID NO 28
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 28
actcggtctc tagcaatttc                                                 20

<210> SEQ ID NO 29
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 29
gtattatact catggttcaa ggtg                                            24

<210> SEQ ID NO 30
<211> LENGTH: 23
```

```
<212> TYPE: DNA
<213> ORGANISM: Artificial Sequence
<220> FEATURE:
<223> OTHER INFORMATION: oligonucleotide primer

<400> SEQUENCE: 30
gtgtaggtaa caaacttgta agg                                           23

<210> SEQ ID NO 31
<211> LENGTH: 21
<212> TYPE: RNA
<213> ORGANISM: Artificial Sequence
<220> FEATURE:
<223> OTHER INFORMATION: si RNA

<400> SEQUENCE: 31
ggacaagcug gacguuaaau u                                             21

<210> SEQ ID NO 32
<211> LENGTH: 21
<212> TYPE: RNA
<213> ORGANISM: Artificial Sequence
<220> FEATURE:
<223> OTHER INFORMATION: Si RNA

<400> SEQUENCE: 32
uuuaacgucc agcuuguccu u                                             21

<210> SEQ ID NO 33
<211> LENGTH: 21
<212> TYPE: RNA
<213> ORGANISM: Artificial Sequence
<220> FEATURE:
<223> OTHER INFORMATION: Si RNA

<400> SEQUENCE: 33
gggcggagcu aaaguugcau u                                             21

<210> SEQ ID NO 34
<211> LENGTH: 21
<212> TYPE: RNA
<213> ORGANISM: Artificial Sequence
<220> FEATURE:
<223> OTHER INFORMATION: Si RNA

<400> SEQUENCE: 34
ugcaacuuua gcuccgcccu u                                             21

<210> SEQ ID NO 35
<211> LENGTH: 21
<212> TYPE: RNA
<213> ORGANISM: Artificial Sequence
<220> FEATURE:
<223> OTHER INFORMATION: si RNA

<400> SEQUENCE: 35
gaacaagguu aaagccgagu u                                             21

<210> SEQ ID NO 36
<211> LENGTH: 21
<212> TYPE: RNA
<213> ORGANISM: Artificial Sequence
<220> FEATURE:
<223> OTHER INFORMATION: Si RNA

<400> SEQUENCE: 36
```
cucggcuuua accuuguucu u                                     21

<210> SEQ ID NO 37
<211> LENGTH: 21
<212> TYPE: RNA
<213> ORGANISM: Artificial Sequence
<220> FEATURE:
<223> OTHER INFORMATION: Si RNA

<400> SEQUENCE: 37
gagcugaacu acuuugcaau u                                     21

<210> SEQ ID NO 38
<211> LENGTH: 21
<212> TYPE: RNA
<213> ORGANISM: Artificial Sequence
<220> FEATURE:
<223> OTHER INFORMATION: Si RNA

<400> SEQUENCE: 38
uugcaaagua guucagcucu u                                     21

<210> SEQ ID NO 39
<211> LENGTH: 21
<212> TYPE: RNA
<213> ORGANISM: Artificial Sequence
<220> FEATURE:
<223> OTHER INFORMATION: Si RNA

<400> SEQUENCE: 39
gaagcaugac ggacaaguau u                                     21

<210> SEQ ID NO 40
<211> LENGTH: 21
<212> TYPE: RNA
<213> ORGANISM: Artificial Sequence
<220> FEATURE:
<223> OTHER INFORMATION: Si RNA

<400> SEQUENCE: 40
uacuuguccg ucaugcuucu u                                     21

<210> SEQ ID NO 41
<211> LENGTH: 21
<212> TYPE: RNA
<213> ORGANISM: Artificial Sequence
<220> FEATURE:
<223> OTHER INFORMATION: Si RNA

<400> SEQUENCE: 41
ggccuuaucc ugccugguau u                                     21

<210> SEQ ID NO 42
<211> LENGTH: 21
<212> TYPE: RNA
<213> ORGANISM: Artificial Sequence
<220> FEATURE:
<223> OTHER INFORMATION: Si RNA

<400> SEQUENCE: 42
uaccaggcag gauaaggccu u                                     21

<210> SEQ ID NO 43
<211> LENGTH: 21
<212> TYPE: RNA
<213> ORGANISM: Artificial Sequence

```
-continued

<220> FEATURE:
<223> OTHER INFORMATION: Si RNA

<400> SEQUENCE: 43
uaacuacacc gaggaaaugu u                                              21

<210> SEQ ID NO 44
<211> LENGTH: 21
<212> TYPE: RNA
<213> ORGANISM: Artificial Sequence
<220> FEATURE:
<223> OTHER INFORMATION: Si RNA

<400> SEQUENCE: 44 cauuccucg guguaguuau u                                               21

<210> SEQ ID NO 45
<211> LENGTH: 21
<212> TYPE: RNA
<213> ORGANISM: Artificial Sequence
<220> FEATURE:
<223> OTHER INFORMATION: Si RNA

<400> SEQUENCE: 45
caagcaaggg ugugaguuuu u                                              21

<210> SEQ ID NO 46
<211> LENGTH: 21
<212> TYPE: RNA
<213> ORGANISM: Artificial Sequence
<220> FEATURE:
<223> OTHER INFORMATION: Si RNA

<400> SEQUENCE: 46
aaacucacac ccuugcuugu u                                              21
```